(12) United States Patent
Kim et al.

(10) Patent No.: US 11,214,781 B2
(45) Date of Patent: Jan. 4, 2022

(54) ENGINEERED ENZYME

(71) Applicant: Inscripta, Inc., Boulder, CO (US)

(72) Inventors: Juhan Kim, Boulder, CO (US); Benjamin Mijts, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/374,628

(22) Filed: Jul. 13, 2021

(65) Prior Publication Data

US 2021/0340513 A1 Nov. 4, 2021

Related U.S. Application Data

(63) Continuation-in-part of application No. 16/953,253, filed on Nov. 19, 2020, which is a continuation of application No. 16/844,079, filed on Apr. 9, 2020, now Pat. No. 10,876,102, which is a continuation of application No. 16/798,315, filed on Feb. 22, 2020, now Pat. No. 10,640,754, which is a continuation of application No. 16/658,948, filed on Oct. 21, 2019, now Pat. No. 10,604,746.

(60) Provisional application No. 62/748,668, filed on Oct. 22, 2018.

(51) Int. Cl.
*C12N 9/22* (2006.01)

(52) U.S. Cl.
CPC ..................... *C12N 9/22* (2013.01)

(58) Field of Classification Search
CPC .......................................... C12N 9/22
USPC ......................................... 435/196
See application file for complete search history.

(56) References Cited

U.S. PATENT DOCUMENTS

| | | |
|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf, III |
| 2004/0110253 A1 | 6/2004 | Kappler et al. |
| 2007/0020761 A1 | 1/2007 | Yu et al. |
| 2010/0076057 A1 | 3/2010 | Sontheimer et al. |
| 2011/0294217 A1 | 12/2011 | McConnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrangou et al. |
| 2017/0022499 A1 | 1/2017 | Lu et al. |
| 2017/0051310 A1 | 2/2017 | Doudna et al. |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

(Continued)

*Primary Examiner* — Tekchand Saidha

(74) *Attorney, Agent, or Firm* — Sarah Brashears; Dianna L. DeVore

(57) ABSTRACT

The present disclosure provides a novel catalytically inactive MAD7 nuclease (dMAD7) that retains the ability to bind DNA in a sequence-specific manner. The MAD7 nuclease from which the dMAD7 has been derived was isolated from *Eubacterium rectale*.

3 Claims, No Drawings

Specification includes a Sequence Listing.

(56) References Cited

U.S. PATENT DOCUMENTS

| | | |
|---|---|---|
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2019/0017072 A1 | 1/2019 | Ditommaso et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0263197 A1 | 8/2020 | Cheng et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO2016/110453 | 7/2016 |
| WO | WO 2016/110453 | 7/2016 |
| WO | WO 2017/053902 | 3/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO2017/216392 | 12/2017 |
| WO | WO 2017/223330 | 12/2017 |
| WO | WO2017/223330 | 12/2017 |
| WO | WO 2018/031950 | 2/2018 |
| WO | WO 2018/071672 | 4/2018 |
| WO | WO 2018/083339 | 5/2018 |
| WO | WO 2018/191715 | 10/2018 |
| WO | WO2019/006436 | 1/2019 |
| WO | WO 2019/200004 | 10/2019 |
| WO | WO2019/209926 | 10/2019 |
| WO | WO 2020/005383 | 1/2020 |
| WO | WO2020/021045 | 1/2020 |

OTHER PUBLICATIONS

Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpf1 enables fast and simple genome editing of *Saccaramyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologies", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Miller et al., "A Tale nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.

(56) References Cited

OTHER PUBLICATIONS

International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.

Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols fortheir delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864.ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR guides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.

SEQUENCE LISTING

```
<160> NUMBER OF SEQ ID NOS: 2

<210> SEQ ID NO 1
<211> LENGTH: 1263
<212> TYPE: PRT
<213> ORGANISM: Eubacterium rectale

<400> SEQUENCE: 1

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
```

-continued

```
                245                 250                 255
Gly Lys Val Asn Ser Phe Met Asn Leu Tyr Cys Gln Lys Asn Lys Glu
            260                 265                 270
Asn Lys Asn Leu Tyr Lys Leu Gln Lys Leu His Lys Gln Ile Leu Cys
        275                 280                 285
Ile Ala Asp Thr Ser Tyr Glu Val Pro Tyr Lys Phe Glu Ser Asp Glu
    290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
                325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
        355                 360                 365
His Tyr Asn Asn Ile Leu Pro Gly Asn Gly Lys Ser Lys Ala Asp Lys
    370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
        435                 440                 445
Leu Lys Ala Ser Glu Leu Lys Asn Val Leu Asp Val Ile Met Asn Ala
    450                 455                 460
Phe His Trp Cys Ser Val Phe Met Thr Glu Gly Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Lys Pro
            500                 505                 510
Tyr Ser Thr Lys Lys Ile Lys Leu Asn Phe Gly Ile Pro Thr Leu Ala
        515                 520                 525
Asp Gly Trp Ser Lys Ser Lys Glu Tyr Ser Asn Asn Ala Ile Ile Leu
    530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
        595                 600                 605
Ser Ala Tyr Ile Leu Glu Gly Tyr Lys Gln Asn Lys His Ile Lys Ser
    610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
            660                 665                 670
```

```
Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
690                 695                 700

Tyr Asn Lys Asp Phe Ser Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Gly Phe Ile Asn Asp Arg Ile Leu Gln Tyr
850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Val Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080
```

```
Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Arg Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 2
<211> LENGTH: 1263
<212> TYPE: PRT
<213> ORGANISM: Eubacterium rectale

<400> SEQUENCE: 2

Met Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
                100                 105                 110

Phe Ala Asn Asp Asp Arg Phe Lys Asn Met Phe Ser Ala Lys Leu Ile
            115                 120                 125

Ser Asp Ile Leu Pro Glu Phe Val Ile His Asn Asn Tyr Ser Ala
    130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
                180                 185                 190
```

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Gln Lys Leu His Lys Gln Ile Leu Cys
                275                 280                 285

Ile Ala Asp Thr Ser Tyr Glu Val Pro Tyr Lys Phe Glu Ser Asp Glu
        290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
        370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
        450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
        530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
        595                 600                 605

-continued

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Lys Asp Gln Phe Gly Asn Ile Gln Ile Val
770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
850                 855                 860

Ile Ala Lys Glu Lys Asp Leu His Val Ile Gly Ile Ala Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Asp Lys Leu Lys Asn Val
    1010                1015                1020

Gly His Gln Cys Gly Cys Ile Phe Tyr Val Pro Ala Ala Tyr Thr

-continued

```
                    1025                1030                1035
Ser Lys Ile Asp Pro Thr Thr Gly Phe Val Asn Ile Phe Lys Phe
        1040                1045                1050

Lys Asp Leu Thr Val Asp Ala Lys Arg Glu Phe Ile Lys Lys Phe
        1055                1060                1065

Asp Ser Ile Arg Tyr Asp Ser Glu Lys Asn Leu Phe Cys Phe Thr
        1070                1075                1080

Phe Asp Tyr Asn Asn Phe Ile Thr Gln Asn Thr Val Met Ser Lys
        1085                1090                1095

Ser Ser Trp Ser Val Tyr Thr Tyr Gly Val Arg Ile Lys Arg Arg
        1100                1105                1110

Phe Val Asn Gly Arg Phe Ser Asn Glu Ser Asp Thr Ile Asp Ile
        1115                1120                1125

Thr Lys Asp Met Glu Lys Thr Leu Glu Met Thr Asp Ile Asn Trp
        1130                1135                1140

Arg Asp Gly His Asp Leu Arg Gln Asp Ile Ile Asp Tyr Glu Ile
        1145                1150                1155

Val Gln His Ile Phe Glu Ile Phe Arg Leu Thr Val Gln Met Arg
        1160                1165                1170

Asn Ser Leu Ser Glu Leu Glu Asp Arg Asp Tyr Asp Arg Leu Ile
        1175                1180                1185

Ser Pro Val Leu Asn Glu Asn Asn Ile Phe Tyr Asp Ser Ala Lys
        1190                1195                1200

Ala Gly Asp Ala Leu Pro Lys Asp Ala Asp Ala Asn Gly Ala Tyr
        1205                1210                1215

Cys Ile Ala Leu Lys Gly Leu Tyr Glu Ile Lys Gln Ile Thr Glu
        1220                1225                1230

Asn Trp Lys Glu Asp Gly Lys Phe Ser Arg Asp Lys Leu Lys Ile
        1235                1240                1245

Ser Asn Lys Asp Trp Phe Asp Phe Ile Gln Asn Lys Arg Tyr Leu
        1250                1255                1260
```

ENGINEERED ENZYME

RELATED CASES

The present application is a continuation-in-part of U.S. Ser. No. 16/953,253, entitled "Engineered Enzymes," filed 19 Nov. 2020; which is a continuation of U.S. Ser. No. 16/844,079, filed 9 Apr. 2020, now U.S. Pat. No. 10,876,102; which is a continuation of U.S. Ser. No. 16/798,315, filed 22 Feb. 2020, now U.S. Pat. No. 10,640,754; which is a continuation of U.S. Ser. No. 16/658,948, filed 21 Oct. 2019, now U.S. Pat. No. 10,604,746; which claims priority to U.S. Provisional Application No. 62/748,668, filed 22 Oct. 2018.

FIELD OF THE INVENTION

This invention relates to a catalytically in active MAD7 variant derived from the bacterium *Eubacterium rectale*.

INCORPORATION BY REFERENCE

Submitted with the present application is an electronically filed sequence listing via EFS-Web as an ASCII formatted sequence listing, entitled "INSCO29CIP_seqlist_20210713", created Jul. 13, 2021, and 22,000 bytes in size. The sequence listing is part of the present specification and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence, hence gene function. These nucleases include nucleic acid-guided nucleases. The range of target sequences that nucleic acid-guided nucleases can recognize, however, is constrained by the need for a specific PAM to be located near the desired target sequence. PAMs are short nucleotide sequences recognized by a gRNA/nuclease complex where this complex directs editing of the target sequence. The precise PAM sequence and pam length requirements for different nucleic acid-guided nucleases vary; however, PAMs typically are 2-7 base-pair sequences adjacent or in proximity to the target sequence and, depending on the nuclease, can be 5' or 3' to the target sequence. Screening the natural diversity of nucleic acid-guided nucleases that exist across species may allow for the discovery of enzymes with enhanced nuclease activity or increased cleavage fidelity when used in a given organism; both changes that may increase the versatility of a nucleic acid-guided nuclease for certain editing tasks.

There is a need in the art of nucleic acid-guided nuclease gene editing for catalytically inactive nucleases with which retain the ability to bind DNA in a sequence-specific manner. The novel dMAD7 enzyme derived from the bacterium *Eubacterium rectale* described herein satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides a novel catalytically inactive MAD7 nuclease (dMAD7) that retains the ability to bind DNA in a sequence-specific manner. The MAD7 nuclease from which the dMAD7 has been derived was isolated from *Eubacterium rectale* (SEQ ID NO: 1) (see, e.g., U.S. Pat. Nos. 9,982,279 and 10,337,028). dMAD7 (SEQ ID NO: 1) differs from MAD7 (SEQ ID NO: 1) by a single amino acid D877A.

Thus, in one embodiment there is provided a catalytically inactive MAD7 enzyme derived from the bacterium *Eubacterium rectale* (dMAD7) having the amino acid sequence of SEQ ID NO: 2. In some aspects, the dMAD7 binds to a bacterial genome. In other aspects, the dMAD7 binds to a yeast genome. In yet other aspects, the dMAD7 binds to the genome of mammalian cells.

These aspects and other features and advantages of the invention are described below in more detail.

DETAILED DESCRIPTION

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series*

(Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W. H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; Berg et al. (2002) *Biochemistry*, $5^{th}$ Ed., W. H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols, Lindgren and Charpentier*, 2015; both of which are herein incorporated in their entirety by reference for all purposes. Basic methods for enzyme engineering may be found in, *Enzyme Engineering Methods and Protocols*, Samuelson, ed., 2013; *Protein Engineering*, Kaumaya, ed., (2012); and Kaur and Sharma, "*Directed Evolution: An Approach to Engineer Enzymes*", Crit. Rev. Biotechnology, 26: 165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region— the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" or "crRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems

Nucleic acid-guided nucleases have been used to engineer the genomes of diverse organisms; however, differences in intrinsic DNA cutting activity, protein expression levels, cellular toxicity and activity in different organisms remain significant challenges that necessitates the screening of many candidate enzymes for editing in each organism. Nucleic acid-guided nucleases with demonstrated activity in vitro and/or in vivo in bacteria, fungi, or mammalian cells are therefore of great utility. The present disclosure provides a novel catalytically inactive MAD7 enzyme (dMAD7) that retains the ability to bind DNA in a sequence-specific manner. The MAD7 nuclease from which the dMAD7 has been derived was isolated from *Eubacterium rectale* (MAD7 nuclease amino acid sequence is SEQ ID NO: 1) (see, e.g., U.S. Pat. Nos. 9,982,279 and 10,337,028). The catalytically inactive MAD7 enzyme has the amino acid sequence of SEQ ID NO: 2. In some aspects, the dMAD7 binds to a bacterial genome. In other aspects, the dMAD7 binds to a yeast genome. In yet other aspects, the dMAD7 binds to the genome of mammalian cells.

Typically, a nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby.

The novel MAD-series nucleases may be delivered to cells to be edited as a polypeptide; alternatively, a polynucleotide sequence encoding the novel MAD-series nuclease(s) is transformed or transfected into the cells to be edited. The polynucleotide sequence encoding the novel MAD-series nuclease may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the novel MAD-series nuclease to be employed depends on many factors, such as what type of edit is to be made in the target sequence and whether an appropriate PAM is located close to the desired target sequence. The novel MAD-series nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

In general, a guide nucleic acid (e.g., gRNA), also called a CRISPR RNA (e.g., crRNA), complexes with a compatible nucleic acid-guided nuclease and can then hybridize with a target sequence, thereby directing the nuclease to the target sequence. The gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a proto spacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments—such as embodiments where cell selection is employed—the promoter driving transcription of the gRNA and the donor nucleic acid (or driving more than one gRNA/donor nucleic acid pair) is an inducible promoter. Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Ser. No. 16/399,988, filed 30 Apr. 2019; U.S. Ser. No. 16/454,865, filed 26 Jun. 2019; and U.S. Ser. No. 16/540,606, filed 14 Aug. 2019. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes a novel MAD-series nuclease comprising one or more nuclear localization sequences (NLSs), such as about or more than about 1, 2, 3, 4, 5, 6, 7, 8, 9, 10, or more NLSs. In some embodiments, the novel nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the novel MAD-series nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12): 5547-5551 (1992)), the Lac Switch Inducible system (Wyborski et al., Environ Mol Mutagen, 28(4): 447-58 (1996); DuCoeur et al., Strategies 5(3): 70-72 (1992); U.S. Pat. No. 4,833,080), the ecdysone-inducible gene expression system (No et al., PNAS, 93(8): 3346-3351 (1996)), the cumate gene-switch system (Mullick et al., BMC Biotechnology, 6: 43 (2006)), and the tamoxifen-inducible gene expression (Zhang et al., Nucleic Acids Research, 24: 543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the novel MAD-series nuclease (e.g., the cells may have already been transformed with an engine vector or the coding sequence for the novel MAD-series nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Pat. Nos. 10,253,316; 10,329,559; 10,323,242; 10,421,959; 10,453,713 and 10,851,389.

After the cells are transformed with the components necessary to perform nucleic acid-guided nuclease editing, the cells are cultured under conditions that promote editing. For example, if constitutive promoters are used to drive transcription of the catalytically inactive dMAD7 nuclease and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, dMAD7, or, in the case of bacteria, a recombineering system—the cells are subjected to inducing conditions.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A catalytically inactive CRISPR nuclease obtained from *Eubacterium* rectale MAD7 (dMAD7) having the amino acid sequence SEQ ID NO: 2 that retains the ability for sequence specific binding a bacteria genome.

2. The catalytically inactive CRISPR nuclease of claim 1 for sequence-specific binding a yeast genome.

3. The catalytically inactive CRISPR nuclease of claim 1 for sequence-specific binding an isolated mammalian cell genome.

* * * * *